United States Patent [19]

Siri

[11] Patent Number: Plant 5,954

[45] Date of Patent: Apr. 21, 1987

[54] MINIATURE CARNATION—ROSE

[75] Inventor: Angelo J. Siri, San Francisco, Calif.

[73] Assignee: Siri Brothers Nursery, Inc., Palo Alto, Calif.

[21] Appl. No.: 641,923

[22] Filed: Aug. 17, 1984

[51] Int. Cl.[4] ..... A01H 5/00

[52] U.S. Cl. ..... Plt./71

[58] Field of Search ..... Plt./70–72

*Primary Examiner*—Robert E. Bagwill

[57] ABSTRACT

A miniature carnation plant having blossoms which have a bright but soft, medium-pink color.

2 Drawing Figures

BACKGROUND OF THE NEW PLANT

This invention comprises a new and distinct miniature carnation variety that has its own set of characteristics that set it apart from all other varieties of miniature carnations. The newly discovered variety, called "Rose," originated as a sport of a seedling, 33K5, an unpatented variety.

The botanical classification of the new variety is *Dianthus caryophyllus longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif., by taking cuttings. The cuttings so taken and grown have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
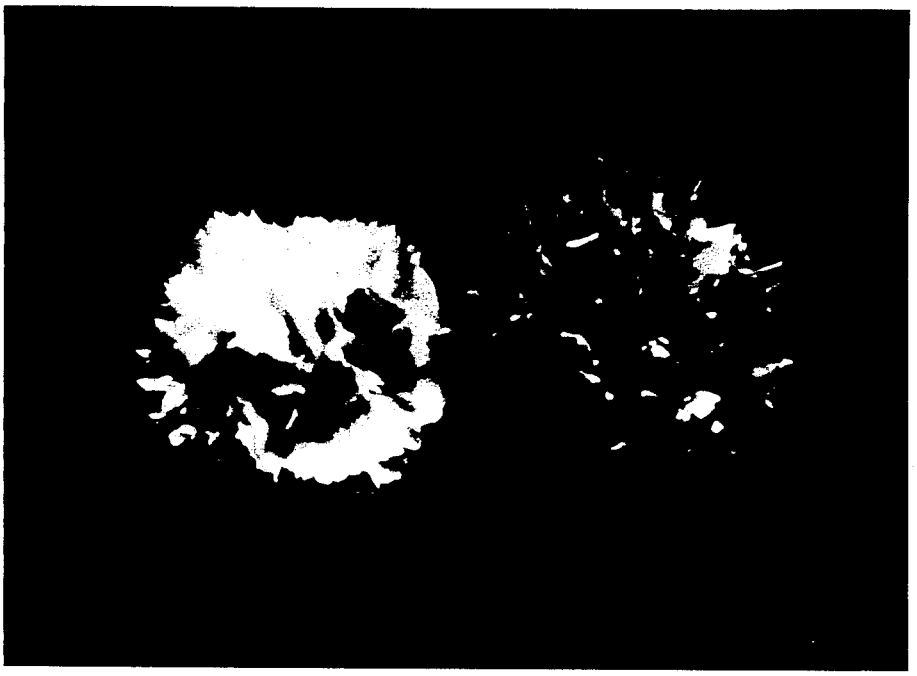
FIG. 1 is an enlarged view of the flower of the new variety Rose on the right and showing the parent, a seedling 33K5, on the left.
Figure 2:
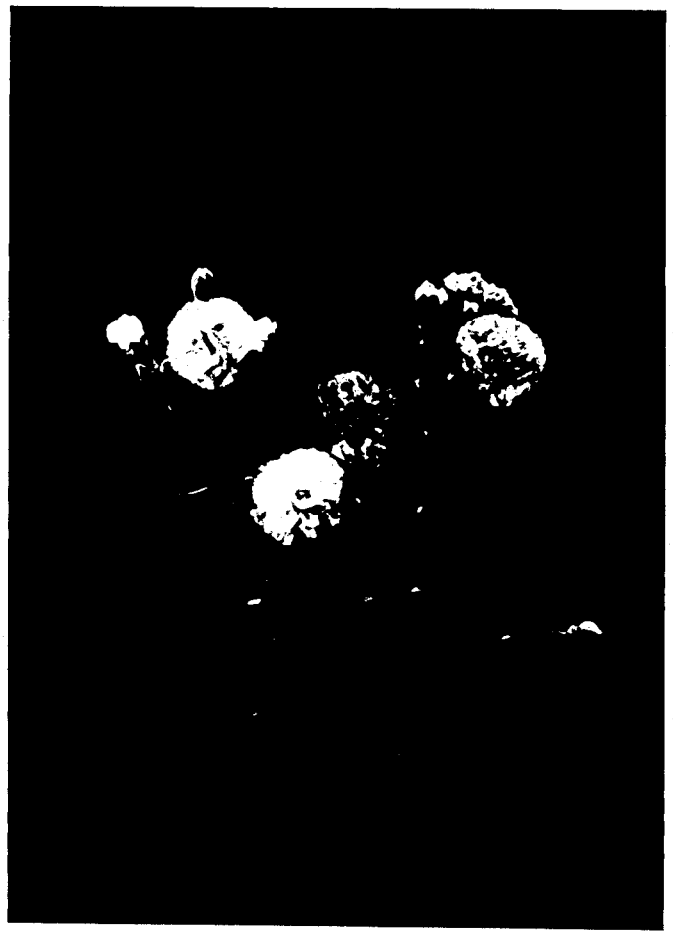
FIG. 2 is a view of the sprays of the new variety Rose on the right and the prior art 33K5 on the left.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "R.H.S." for The Royal Horticultural Colour Chart, The Royal Horticultural Society, London, England.

Growth habits

Height: Average — medium height.
Foliage: Average.
Speed of growth: Average.

Root system: Average.

Foliage

Leaf size:
*Length.*—Average at midstem is $3\frac{3}{4}''$.
*Width.*—Average at midstem is $\frac{3}{8}''$.
Features.—N/A.
Leaf shape: Average curl with a long accuminating tip.
Leaf texture: Smooth and leathery.
Leaf color:
*Upperside.*—R.H.S. Green Group 137C with a whitish color over the green.
*Underside.*—R.H.S. Green Group 137C with a whitish color over the green.
Leaf ribs: One rib down the center from the base to the tip of the leaf.
Leaf habit: Average curl.
Leaf density: Average.

Stem

Stem strength: Stronger than average.
Stem color: R.H.S. Green Group 137C with a whitish color over the green.
Nodes: Average.
*Space between nodes.*—$3\frac{3}{4}''$ at midstem.
Stem branching: Very good not clubby, wide spaces between branches.

Buds

Bud shape: Oval.
Bud color: The top half of the bud is LCC H-22 L-1 and the bottom half blends into LCC H-22 L-9.
Uniformity of bud opening: Not real uniform — one tends to mature before the others.
Bud splitting: Very seldom.
Number of sepals per calyx: 3% of the calyxs have 4. 27% of the calyxs have 6. 70% of the calyxs have 5.

Flower

Description of the color of the bloom: The color of the bloom is a medium pink, LCC H-38 L-6. The edges of the petals will sometimes fade in the summer.
General tonality of the color: Bright with a softness to it.
Diameter of average bloom: $1\frac{3}{4}$–$2''$.
Bloom shape: Generally round with a high center and flat outer petals.
Keeping quality: Average.
Fragrance: Very slight.

Petalage

Petal texture: Soft and smooth.
Petal edge: Very serated.
Color stability: Extremely stable.
Petal size: Average length at midstem $1\frac{1}{2}''$. Average width at widest point at midstem $\frac{7}{8}''$.
Calyx color: The top half is LCC H-22 L-1, the bottom half blends into LCC H-22 L-9, the tips of the leaves at the bottom of the calyx are LCC H-20 L-14.

Reproductive organs

Stamen: Both with and without anthers.
Average length of stamen: $\frac{3}{4}''$ to 1″ both with and without anthers.
Color of anthers: LCC H-26 L-2.
Color of filament: A transparent color similar to LCC H-22 L-1.
Pistils:
*Shape.*—Approximately 80% have 2 styles and 20% have 3 styles.
*Number.*—1.
*Length from tip to ovary.*—Approximately 1″.
Stigma:
*Shape.*—Round.
*Color.*—White.

Style:
*Color.*—LCC H-25 L-1.
Ovary:
*Shape.*—Ovid.
*Color.*—The tip is LCC H-25 L-11, the midle is LCC H-24 L-9, the bottom is LCC H-23 L-2.
*Length.*—Approximately $\frac{3}{8}''$.
*Width.*—Approximately 3/16″.

Distinguishing Characteristics Between the New Variety and Parent

The distinguishing characteristic between the new variety and the parent is the color. The parent is an orange while the new variety is a medium pink shade.

Similar Characteristics of the New Variety and Parent

All of the characteristics of both varieties are similar except for the distinguishing characteristics referred to above.

Years of asexual reproduction: 1979, 1980, 1981, 1982, 1983.

I claim:

1. A new and distinct variety of miniature carnation plant, substantially as herein shown and described.

* * * * *